US009320775B2

(12) United States Patent
McNulty et al.

(10) Patent No.: US 9,320,775 B2
(45) Date of Patent: Apr. 26, 2016

(54) USE OF NUCLEIC ACIDS WITH REDUCED PRESSURE THERAPY

(75) Inventors: Amy McNulty, San Antonio, TX (US); Kristine Kieswetter, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 889 days.

(21) Appl. No.: 12/433,047

(22) Filed: Apr. 30, 2009

(65) Prior Publication Data

US 2009/0275884 A1 Nov. 5, 2009

Related U.S. Application Data

(60) Provisional application No. 61/049,283, filed on Apr. 30, 2008.

(51) Int. Cl.
| | |
|---|---|
| *A61F 13/00* | (2006.01) |
| *A61M 1/00* | (2006.01) |
| *C07H 21/04* | (2006.01) |
| *A61K 38/17* | (2006.01) |
| *A61K 31/7088* | (2006.01) |
| *A61K 48/00* | (2006.01) |

(52) U.S. Cl.
CPC .......... *A61K 38/1709* (2013.01); *A61K 31/7088* (2013.01); *A61K 48/0083* (2013.01); *A61M 1/0084* (2013.01); *A61M 1/0088* (2013.01); *A61F 13/00* (2013.01); *A61F 2013/00089* (2013.01); *A61K 48/005* (2013.01); *C07H 21/04* (2013.01)

(58) Field of Classification Search
CPC . A61K 48/00; A61K 38/1825; A61K 48/005; A61F 2013/00157; A61F 2013/00519; A61F 2002/3084; A61F 13/00; A61F 2013/00089; A61M 1/0084; A61M 1/0088; C07H 21/04
USPC ........... 514/44 R; 536/23.5, 24.1; 602/46, 47; 604/35
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |

(Continued)

FOREIGN PATENT DOCUMENTS

| | | |
|---|---|---|
| AU | 550575 A1 | 8/1982 |
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |

(Continued)

OTHER PUBLICATIONS

Stroncek et al, Reichert WM, editor. Indwelling Neural Implants: Strategies for Contending with the In Vivo Environment. Boca Raton (FL): CRC Press; 2008.*

(Continued)

*Primary Examiner* — Shin Lin Chen (57) ABSTRACT

Provided is a method of treating a wound site. Also provided is a system for treating a wound site. Additionally provided is the use of reduced pressure and a nucleic acid that promotes wound healing for treatment of a wound site. Further provided is the use of a nucleic acid that promotes wound healing for the manufacture of a medicament for treating a wound site that is undergoing reduced pressure treatment.

5 Claims, 2 Drawing Sheets

(56) References Cited

U.S. PATENT DOCUMENTS

| | | | |
|---|---|---|---|
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,013,516 A * | 1/2000 | Verma et al. | 435/325 |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2005/0136125 A1* | 6/2005 | Roth | 424/600 |
| 2007/0021698 A1 | 1/2007 | Fleischmann | |
| 2007/0185426 A1 | 8/2007 | Ambrosio et al. | |
| 2007/0191273 A1 | 8/2007 | Ambati et al. | |
| 2008/0275409 A1 | 11/2008 | Kane et al. | |

FOREIGN PATENT DOCUMENTS

| | | | |
|---|---|---|---|
| EP | 0117632 A2 | 9/1984 | |
| EP | 0161865 A2 | 11/1985 | |
| EP | 0358302 A2 | 3/1990 | |
| EP | 1018967 B1 | 8/2004 | |
| GB | 692578 | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 333 965 A | 8/1999 | |
| GB | 2 329 127 B | 8/2000 | |
| JP | 4129536 | 4/1992 | |
| SG | 71559 | 4/2002 | |
| WO | WO 80/02182 | 10/1980 | |
| WO | WO 87/04626 | 8/1987 | |
| WO | WO 90/10424 | 9/1990 | |
| WO | WO 93/09727 | 5/1993 | |
| WO | WO 94/20041 | 9/1994 | |
| WO | WO 96/05873 | 2/1996 | |
| WO | WO 97/18007 | 5/1997 | |
| WO | WO 99/13793 | 3/1999 | |
| WO | WO 99/54456 A1 | 10/1999 | |
| WO | WO-00/59424 A | 10/2000 | |
| WO | WO 03/029406 | * | 4/2003 |
| WO | WO 2006/083182 A1 | 8/2006 | |
| WO | WO 2006/134494 A2 | 12/2006 | |
| WO | WO-2007/031762 A | 3/2007 | |
| WO | WO 2008/057600 A | 5/2008 | |
| WO | WO-2009/006226 A | 1/2009 | |

OTHER PUBLICATIONS

Yang et al, Zhonghua Wai Ke Za Zhi, 2012, 50:650-654.*
Boudreau et al., 2003, US 20030109450 A1.*
Morykwas et al., 1997, Annals of Plastic Surgery, vol. 38(6), p. 553-562.*
Arbeit, Jefferey, 2005, U.S. Pat. No. 6,838,430 B2.*
Vogel, Richard, 2007, US 20070299563 A1.*
N.A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61(1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

(56) References Cited

OTHER PUBLICATIONS

Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.
G. Živadinović, V. Ðukić, Ž. Maksimović, Ð. Radak, and P. Peška, "Vacuum Therapy in the Treatment of Peripheral Blood Vessels," *Timok Medical Journal* 11 (1986), pp. 161-164 (certified translation).
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax," *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
International Search Report and Written Opinion date mailed Dec. 2, 2009; PCT International Application No. PCT/US2009/042232.
Derrick, Kathleen et al: "Comparative analysis of global gene expression profiles between diabetic rat wounds treated with vacuum-assisted closure therapy, moist wound healing or gauze under suction" International Wound Journal Dec. 2008, vo.. 5, No. 5, pp. 615-624, XP002555279, ISSN: 1742-481X.
Grimm et al. "Expression of HIF-1α in Irradiated Tissue is Altered by Topical Negative-Pressure Therapy"; Strahlenther Onkol 2007, No. 3, Urban & Vogel; pp. 144-149.
Kane et al. "Controlled Induction of Distributed Microdeformation in Wounded Tissue via a Microchamber Array Dressing", pp. 333-340; Journal of Biomedical Materials Research; Nov. 2010, vol. 95A, Issue 2.
V.A.C.® Therapy Clinical Guidelines: A Reference Source for Clinicians (Jul. 2007).
Andros G, Armstrong DG, Attinger CE, Boulton AJ, Frykberg RG, Joseph WS, et al. "Consensus statement on negative pressure wound therapy (V.A.C. Therapy) for the management of diabetic foot wounds." Wounds 18[6], S1-S32. 2006.
Armstrong DG, Jude EB. "The role of matrix metalloproteinases in wound healing." J Am Podiatr Med Assoc. 92[1], 12-18. 2002.
Armstrong DG, Lavery LA, Diabetic Foot Study Consortium. "Negative pressure wound therapy after partial diabetic foot amputation: a multicentre, randomised controlled trial." Lancet 366[9498], 1704-1710. 2005.
Benjamini Y, Hochberg Y. Controlling the false discovery rate: "A practical and powerful approach to multiple testing." Royal Statistical Soc Jan. 1, 1993;57(1):289-300.
Bolstad BM, Irizarry RA, Astrand M, Speed TP. "A comparison of normalization methods for high density oligonucleotide array data based on variance and bias." Bioinformatics Jan. 22, 2003;19(2):185-93.
Brem H, Sheehan P, Rosenberg HJ, Schneider JS, Boulton AJM. "Evidence-based protocol for diabetic foot ulcers." Plast Reconstr Surf 117, 193S-209S. 2006.
Bunka D and Stockley PG. "Aptamers come of age—at last." Nat. Rev. Microbiol. 4, 588-596. 2006.
Centers for Disease Control National Diabetes Fact Sheet. CDC Web Site. Available at: cdc.gov/diabetes; 2007.
Clark JB, Palmer CJ, Shaw WN. "The diabetic Zucker fatty rat." Proc Soc Exp Biol Med 173, 68-75. 1983.
Diegelmann RF, Evans MC. "Wound Healing: An Overview of Acute, Fibrotic and Delayed Healing." Front Biosci Jan. 1, 2004;9:283-9.
DiPietro LA, Burdick M, Low QE, Kunkel SL, Strieter RM. "MIP-1a as a critical macrophage chemoattractant in murine wound repair." J Clin Invest 101[8], 1693-1698. 2007.
Eginton MT, Brown KR, Seabrook GR, Towne JB, Cambria RA. "A prospective randomized evaluation of negative-pressure wound dressings for diabetic foot wounds." Ann Vasc Surg 2003;17(6):645-9.
Frantz S et al. "Innate immunit and angiogenesis." Circ. Res. 96, 15-26. 2005.
Gailit J, Clark RA. "Wound repair in the context of extracellular matrix." Curr Opin Cell Biol 6[5], 717-725. 1994.
Gallucci RM, Simeonova PP, Matheson JM, Kommineni C, Guriel JL, Sugawara T, et al. "Impaired cutaneous wound healing in interleukin-6-deficient and immunosuppressed mice." FASEB J. 14, 2525-2531. 2000.
Goldman R. "Growth factors and chronic wound healing: past, present, and future." Adv Skin Wound Care 2004;17(1):24-35.

(56) References Cited

OTHER PUBLICATIONS

Goren I, Linke A, Muller E, Pfeilschifter J, Frank S. "The suppressor of cytokine signaling-3 is upregulated in impaired skin repair: implications for keratinocyte proliferation." J Invest Dermatol 126, 477-485. 2006.
Harding KG, Morris HL, Patel GK. "Science, medicine and the future: healing chronic wounds." BMJ 324[7330], 160-163. 2002.
IDF. Diabetes Atlas. 3rd ed. Brussels: International Diabetes Federation; 2005a.
IDF. Diabetes and foot care: time to act. Brussels: International Diabetes Federation; 2005b.
Jazag A et al. "Single small-interfering RNA expression vector for silencing multiple transforming growth factor-β pathway components." Nucl. Acids Res. 33, e131. 2005.
Jeffcoate WJ. "The incidence of amputation in diabetes." Acta Chir Belg Apr. 1, 2005;105(2):140-4.
Kampfer H, Muhl H, Manderscheid M, Kalina U, Kauschat D., Pfelschifter J, et al. "Regulation of interleukin-18 (IL-18) expression in keratinocytes (HaCaT): implications for early wound healing." Eur Cytokine Netw 11, 626-633. 2000.
Katsumi A, Naoe T, Matsushits T, Kaibuchi K, Schwartz MA. "Integrin activation and matrix binding mediate cellular responses to mechanical stretch." J Biol Chem 280(17), 16546-16549. 2005.
Kim IY et al. "Transforming growth factor-β:Biology and clinical relevance." J Biochem Mol Biol 38, 1-8. 2005.
Kregel KC. "Heat shock proteins: modifying factors in physiological stress responses and acquired thermotolerance." J Appl Physiol 92, 2177-2186. 2002.
Krützfeldt et al. "Silencing of microRNAs in vivo with 'antagomirs.'" Nature 438, 685-689. 2005.
Li M, Carpio DF, Zheng Y, Bruzzo P, Singh V, Ouaaz F, et al. "An essential role of the NF-kappa B/Toll-like receptor pathway in induction of inflammatory and tissue-repair gene expression by necrotic cells." J Immunol 166[12], 7128-7135. 2001.
Li Q, Fukuda K, Lu Y, Nakamura Y, Chikama T, Kumagai N, et al. "Enhancement by neutrophils of collagen degradation by corneal fibroblasts." J Leukoc Biol 74, 412-419. 2003.
McCallon SK, Knight CA, Valiulus JP, Cunningham MW, McCulloch JM, Farinas LP. "Vacuum-assisted closure versus saline-moistened gauze in the healing of postoperative diabetic foot wounds." Aug. 2000; 46(8): 28-32-34.
McMurtry AL, Cho K, Young UT, Nelson CF, Greenhalgh DG. "Expression of HSP70 in healing wounds of diabetic and nondiabetic mice." J Surg Res 86, 36-41. 1999. Ostomy Wound Manage, Sep. 1999.
Medina A, Scott PG, Ghahary A, Tredget EE. "Pathophysiology of chronic nonhealing wounds." J Burn Care Rehabil 26[4], 306-319. 2005.
Meszaros AJ, Reichner JS, Albina JE. "Macrophage-induced neutrophil apoptosis." J Immunol 2000;165(1):435-41.
Rakoff-Nahoum S, Paglino J, Eslami-Varzaneh F, Edberg S, Medzhitov RM. "Recognition of commensal microflora by toll-like receptors is required for intestinal homeostasis." Cell 118, 229-241. 2004.
Reddi AH. "Cartilage morphogenic proteins: role in joint development, homeostasis, and regeneration." Ann Rheum Dis 62(Suppl II),ii73-ii78. 2003.
Saxena V, Hwang CW, Huang S, Eichbaum Q, Ingber DE, Orgill DP. "Vacuum-assisted closure: microdeformations of wounds and cell proliferation." Plast Reconstr Surg 114[5], 1086-1098. 2004.
Schultz GS, Ladwig G, Wysocki A. "Extracellular matrix: review of its roles in acute and chronic wounds." World Wide Wounds Aug. 1, 2005;1-24.
Searle A, Campbell R, Tallon D, fitzgerald A, Vedhara K. "A qualitative approach to understanding the experience of ulceration and healing in the diabetic foot: Patient and podiatrist perspectives." Wounds 17[1], 16-26. 2005.
Sharman D. "Moist wound healing: a review of evidence, application and outcome—Review." Diabetic Foot 6[3], 112-116. 2003.
Shilo S. et al. "MicroRNA in cutaneous wound healing: A new paradigm." DNA Cell Biol. 26, 227-237. 2007.
Sibbald G, Orsted H, Schultz GS, Coutts P, Keast D. "Preparing the wound bed 2003: Focus on infection and inflammation." Ostomy Wound Manage 49[11], 24-51. 2003.
Smith APS, Kieswetter K, Goodwin AL, McNulty A. "Negative Pressure Wound Therapy." Chronic Wound Care: A clinical source book for healthcare professionals. 4th Edition ed. Malvern: HMP Communications; 2007. p. 271-86.
Stadelmann WK, Digenis AG, Tobin GR. "Physiology and Healing Dynamics of Chronic Cutaneous Wounds." Am J Surg Aug. 24, 1998;176(Suppl 2A):26S-38S.
Thomas PD, Campbell MJ, Kejariwal A, Mi H, Karlak B, Daverman R, et al. "PANTHER: a library of protein families and subfamilies indexed by function." Genome Res Sep. 1, 2003;13(9):2129-41.
Thomas PD, Kejariwal A, Guo N, Mi H, Campbell MJ, Muruganujan A, et al. "Applications for protein sequence-function evolution data: mRNA/protein expression analysis and coding SNP scoring tools." Nucleic Acids Res Jul. 1, 2006;34(Web Server Issue):W645-W650.
Venturi ML, Attinger CE, Mesbahi AN, Hess CL, Graw KS. "Mechanisms and clinical applications of the vacuum-assisted closure (VAC) Device: a review." Am J Clin Dermatol 6[3], 185-194. 2006.
Wu L. et al. "Keratinocyte growth factor induces granulation tissue in ischemic dermal wounds. Importance of epitehlial-mesenchymal cell interactions." Arch Surg 131, 660-666. 1996.
Yager DR, Nwomeh BC. "The proteolytic environment of chronic wounds." Wound Rep Reg 7[6], 433-441. 1999.
Zhou R-H et al. "Vascular endothelial growth factor activation of sterol regulatory element binding protein." Circ. Res. 95, 471-478. 2004.

* cited by examiner

USE OF NUCLEIC ACIDS WITH REDUCED PRESSURE THERAPY

CROSS-REFERENCE TO RELATED APPLICATIONS

This application claims the benefit of U.S. Provisional Application No. 61/049,283, filed Apr. 30, 2008, incorporated by reference.

BACKGROUND OF THE INVENTION

1. Field of the Invention

The present invention relates generally to tissue treatment systems and in particular to use of nucleic acids with reduced pressure therapy for the treatment of wounds.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," "subatmospheric pressure therapy," "vacuum sealing therapy" or "vacuum therapy") provides a number of benefits, including faster healing and increased formulation of granulation tissue. Typically, reduced pressure is applied to tissue through a porous pad or other manifolding device. The porous pad contains pores (also called "cells") that are capable of distributing reduced pressure to the tissue and channeling fluids that are drawn from the tissue. The porous pad often is incorporated into a dressing having other components that facilitate treatment.

Wound healing may be broadly split into three overlapping basic phases: inflammation, proliferation, and maturation. The inflammatory phase is characterized by hemostasis and inflammation. The next phase consists mainly of epithelialization, angiogenesis, granulation tissue formation, and collagen deposition. The final phase includes maturation and remodeling. The complexity of the three step wound healing process is augmented by the influence of local factors such as ischemia, edema, and infection, as well as systemic factors such as diabetes, age, hypothyroidism, malnutrition, and obesity. The rate limiting step of wound healing, however, is often angiogenesis. Wound angiogenesis is marked by endothelial cell migration and capillary formation where the sprouting of capillaries into the wound bed is critical to support the regenerating tissue. The granulation phase and tissue deposition require nutrients supplied by the capillaries. Impairments in wound angiogenesis therefore may lead to chronic problem wounds.

Expression of the angiogenic phenotype is a complex process that requires a number of cellular and molecular events to occur in sequential steps. Some of these activities include endothelial cell proliferation, degradation of surrounding basement membrane, migration of endothelial cells through the connective tissue stroma, formation of tube-like structures, and maturation of endothelial-lined tubes into new blood vessels. Angiogenesis is controlled by positive and negative regulators. In addition to endothelial cells, cells associated with tissue repair, such as platelets, monocytes, and macrophages, release angiogenic growth factors such as vascular endothelial growth factor (VEGF) into injured sites that initiate angiogenesis.

There are currently several methods used to augment wound healing, including irrigating the wound to remove toxins and bacteria, local and systemic administration of antibiotics and anesthetics, and local application of growth factors. One of the most successful ways to promote wound healing in soft tissue wounds that are slow to heal or non-healing is reduced pressure therapy, discussed above.

Although reduced pressure therapy is highly successful in the promotion of wound healing, healing wounds that were previously thought largely untreatable remains difficult. Because the inflammatory process is very unique to the individual, even addition of reduced pressure therapy may not result in a fast enough response for adequate healing. Thus, the wound healing process can be very slow and laborious, which can be inconvenient to the patient and sometimes costly. Thus, it is desirable to find ways to augment reduced pressure therapy to decrease the time that reduced pressure therapy is needed.

SUMMARY OF THE INVENTION

The problems presented by existing wound healing regimes are solved by the systems and methods of the illustrative embodiments described herein. In one embodiment, a method of treating a wound site is provided and includes applying a nucleic acid that promotes wound healing to the wound site, and applying a reduced pressure to the wound site.

In another embodiment, a system for treating a wound at a wound site is provided and includes a distribution manifold; a reduced pressure source fluidly connected to said distribution manifold to deliver reduced pressure to the wound site; and a nucleic acid source fluidly connected to said distribution manifold to deliver nucleic acid to the wound site sufficient to treat the wound.

In still another embodiment, a use of reduced pressure and a nucleic acid is provided that includes their use for treatment of a wound site.

In an additional embodiment, a use of a nucleic acid is provided for the manufacture of a medicament for treating a wound site that is undergoing reduced pressure treatment.

Other objects, features, and advantages of the illustrative embodiments will become apparent with reference to the drawings and detailed description that follow.

DETAILED DESCRIPTION OF PREFERRED EMBODIMENT

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, biological, genetic, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The illustrative embodiments described herein are directed to a system and method for applying reduced pressure at a tissue site. Reduced pressure generally refers to a pressure less than the ambient pressure at a tissue site that is being subjected to treatment. In most cases, this reduced pressure will be less than the atmospheric pressure of the location at which the patient is located. Although the terms "vacuum" and "negative pressure" may be used to describe the pressure applied to the tissue site, the actual pressure applied to the tissue site may be significantly less than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure.

In one embodiment, a method of treating a wound site is provided and includes applying a nucleic acid that promotes wound healing to the wound site, and applying a reduced pressure to the wound site.

Generally, a wound site is a wound or defect located on or within any tissue, including but not limited to, bone tissue, adipose tissue, muscle tissue, neural tissue, dermal tissue, vascular tissue, connective tissue, cartilage, tendons or ligaments. A wound site may also be any tissue that is not necessarily wounded or defected, but instead is an area in which it is desired to add or promote growth of additional tissue.

In some embodiments, the wound site comprises dermal tissue. In other embodiments, the wound site comprises bone tissue. In additional embodiments, the wound site comprises cartilage, tendon, ligament, nerve tissue, or adipose tissue.

It is contemplated that one with skill in the art may use any cell transfection technique to assist the entry of the nucleic acid into the cells at the wound site, depending upon the type and shape of the wound site to be treated. In some embodiments, lipofection is used to deliver the nucleic acid to the cell. In other embodiments, the method of cell transfection includes transfection reagents such as calcium phosphate, liposomes, Lipfectamine, Fugene, jetPEI, highly branched organic compounds such as dendimers, or DreamFect. Alternative techniques of cell transfection include electroporation, microinjection, biolistics, heat shock, magnetofection, and nucleofection. The use of viral vectors comprising the nucleic acid also generally facilitate uptake of the nucleic acid, as is known in the art. In some methods, transfection reagents such as Lipfectamine, Fugene, jetPEI or DreamFect are used to promote the entry of the viral vectors into the cell.

The nucleic acids discussed in the instant invention are at least two nucleotides covalently linked together. Many variants of a nucleic acid may be used for the same purpose as a given nucleic acid. Thus, a nucleic acid also encompasses substantially identical nucleic acids and complements thereof. Nucleic acids may be single stranded or double stranded, or may contain portions of both double stranded and single stranded sequence. A nucleic acid may be DNA (e.g., genomic or cDNA), RNA, or a hybrid, where the nucleic acid may contain combinations of deoxyribo- and ribonucleotides, and combinations of bases including uracil, adenine, thymine, cytosine, guanine, inosine, xanthine, hypoxanthine, isocytosine and isoguanine. Nucleic acids may be obtained by chemical synthesis methods or by recombinant methods. The nucleic acids also include nucleic acid analogs that may have at least one different linkage, e.g., phosphoramidate, phosphorothioate, phosphorodithioate, or O-methylphosphoroamidite linkages. Other analog nucleic acids include those with positive backbones, non-ionic backbones, and non-ribose backbones. Nucleic acids containing one or more non-naturally occurring or modified nucleotide are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that nucleobase-modified ribonucleotides are also suitable. Examples of such ribonucleotides include: ribonucleotides containing a non-naturally occurring nucleobase instead of a naturally occurring nucleobase, such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; and O- and N-alkylated nucleotides, e.g. N6-methyl adenosine. Modifications of the ribose-phosphate backbone may be done for a variety of reasons, e.g., to increase the stability and half-life of such molecules in physiological environments. Mixtures of naturally occurring nucleic acids and analogs may also be made; alternatively, mixtures of different nucleic acid analogs, and mixtures of naturally occurring nucleic acids and analogs may be made.

It is contemplated that, for many embodiments, the nucleic acid encodes a protein that promotes wound healing. For these embodiments, the nucleic acid is a form such that it could be transcribed and possibly translated by the cells in the wound site. For this purpose, the nucleic acid must be operably linked to control elements (e.g., a promoter, poly-A tail, Kozak sequence, enhancer, targeting sequence, termination elements) that directs expression of the protein when the nucleic acid is inside a cell in the wound site. Methods for preparing such nucleic acid constructs are known in the art.

Where the nucleic acid encodes a protein, the protein can be naturally occurring or it can be an artificial protein that does not exist in nature. The naturally occurring protein can be from any source, including any eukaryotic, prokaryotic, or archaeal source. Where the nucleic acid is used for wound healing in a mammal, it is preferred that the protein is a mammalian protein, most preferably from the same species as the mammal. For example, if the nucleic acid is used on a wound site of a human, it is preferred that a protein encoded by the nucleic acid is a human protein.

The nucleic acid can be part of a vector that facilitates uptake and transcription of the nucleic acid. Non-limiting examples of such vectors are naked DNA vectors, plasmids, cosmids, and viruses, for example, retroviruses and adenoviruses.

In some embodiments, the nucleic acid encodes a structural protein. Non-limiting examples of useful structural proteins are collagen, fibronectin, elastin and laminin. In other embodiments, the nucleic acid encodes an enzyme, for example Tie-1, Tie-2 or HIF-1α.

In additional embodiments, the nucleic acid encodes a cytokine. Any cytokine that promotes wound healing can be utilized. Preferred examples include a fibroblast growth factor (FGF), a vascular endothelial growth factor (VEGF), a platelet derived growth factor (PDGF), a transforming growth factor-β (TGFβ), a TGFα, a stem cell factor (SCF), an angiopoietin 1 (Ang1), an epidermal growth factor (EGF), an interleukin, an insulin-like growth factor (IGF), a laminin, a hepatocyte growth factor (HGF), an adrenomedullin, a keratinocyte growth factor (KGF), a bone morphogenic protein (BMP), a cartilage derived morphogenic protein (CDMP), or a placental growth factor (PlGF). (US Patent Publication 20070191273A1; Zhou et al., 2004; Wu et al., 1996; Kim et al., 2005; Reddi, 2003). In some aspects, the cytokine is angiogenic. Non-limiting examples of angiogenic cytokines are bFGF, VEGF-A, TGF-α, SCF, Ang1, laminin-8, HGF, adrenomedullin, and PlGF.

The nucleic acid can also encode an enzyme inhibitor, for example a tissue inhibitor of metalloproteinase. Alternatively, the nucleic acid can encode a cell surface receptor, for example an integrin (PCT Patent Publication WO9954456A1). In additional embodiments, the nucleic acid encodes a transcription factor. Non-limiting examples of useful transcription factors for these embodiments include HoxD3, hypoxia-inducible factor-1α (HIF-1α), and Net.

The Example below describes a global gene expression analysis that identified genes that were differentially expressed during wound healing under reduced pressure. Notably, several genes were identified with significantly increased expression during wound healing under reduced pressure and that likely contribute to wound healing. It is contemplated that those genes are particularly useful as the nucleic acids in the present invention. Thus, in some embodiments, the nucleic acid encodes a protein that increases expression in response to reduced pressure treatment of the wound site. Examples of these proteins are interleukin 6 (IL-6), chemokine ligand 7 (Ccl7), tissue inhibitor of metalloproteinase 1 (TIMP1), integrin alpha M (Itgam), suppressor of cytokine signaling 3 (Socs3), matrix metalloproteinase-8 (MMP-8), macrophage inflammatory protein-1 alpha receptor (MIP1), toll like receptor 1 (TLR1), tumor necrosis factor receptor superfamily member 1b (Tnfrsf1b), heat shock protein 70 (Hsp70), calmodulin-like 3, and keratin complex 1 acidic 14 (Krt1-14).

The nucleic acid used in these methods can also specifically inhibit expression of a protein that inhibits wound healing. Non-limiting examples of proteins that inhibit wound healing are small mothers against decapentaplegic homolog 3 (Smad3), vascular endothelial growth factor receptor 1 (VEGFR1), VEGFR2, VEGFR3, connexin, and myostatin (U.S. Patent Publication 20070191273A1; PCT Patent Publications WO06083182A1 and WO06134494; Jazag et al., 2005; Franz et al., 2005).

In some aspects of these embodiments, the nucleic acid is an antisense nucleic acid specific to an mRNA encoding the protein. Production of such an antisense nucleic acid for any protein target is within the skill of the art.

The nucleic acid for these embodiments can also be a ribozyme specific to an mRNA encoding the protein. Ribozymes that inhibit expression of any protein that inhibits wound healing can be made by a skilled artisan without undue experimentation.

In additional aspects of these embodiments, the nucleic acid is an miRNA specific to an mRNA encoding the protein that inhibits wound healing. As used herein, miRNAs are small endogenously expressed noncoding RNAs that can interact with matching mRNA and base pair to a portion of the mRNA, which results in either degradation of the mRNA or suppression of translation. MiRNA can therefore act as regulators of cellular development, differentiation, proliferation and apoptosis. MiRNAs can modulate gene expression by either impeding mRNA translation, degrading complementary miRNAs, or targeting genomic DNA for methylation. For example, miRNAs can modulate translation of miRNA transcripts by binding to and thereby making such transcripts susceptible to nucleases that recognize and cleave double stranded RNAs.

"MiRNA" includes short interfering nucleic acid (siNA), short interfering RNA (siRNA), and short hairpin RNA (shRNA) molecules. An miRNA of the invention can be unmodified or chemically-modified. An miRNA of the instant invention can also be chemically synthesized, expressed from a vector, or enzymatically synthesized.

Depending upon the embodiment, the miRNA of the instant invention may be included in reagents and/or methods for a variety of therapeutic applications. The miRNA may also be used for diagnostic and target validation applications. The miRNA nucleic acid sequence must have sufficient substantial identity to the mRNA target site to achieve effective inhibition of translation. The target sites in the mRNA may be in the 5' UTR, the 3' UTR or in the coding region. In a preferred embodiment, the miRNA of the instant invention is specific for mRNA to a specific cell type.

While it is understood that the length of the miRNA used in accordance with the invention may be any length which results in effective interaction of the nucleic acid to its target, there are specific embodiments which set forth a preferred length. For example, in one embodiment of the present invention, each sequence of an miRNA of the invention is independently about 18 to about 24 nucleotides in length. In another embodiment, the miRNA or miRNA inhibitor molecule is a duplex independently comprising about 17 to about 23 bases. In yet another embodiment, miRNA or miRNA inhibitor molecules comprise hairpin or circular structures are about 35 to about 55 nucleotides in length.

Naturally occurring miRNA has been implicated in playing a role in numerous diseases and disorders. For example, miRNAs may play a role in diabetes and neurodegeneration associated with Fragile X syndrome, cancer, spinal muscular atrophy, and early on-set Parkinson's disease. Further, several miRNAs are virally encoded and expressed in infected cells (e.g., EBV, HPV and HCV).

In wound healing, VEGF and Tie-1 can apparently be inhibited by naturally occurring miRNA (Shilo et al., 2007). An miRNA inhibitor that inhibits these naturally occurring miRNAs is contemplated as within the scope of the nucleic acids of these methods. The miRNA inhibitors used may be any nucleic acid sequences which can reduce or inhibit production of a specific miRNA or inhibit binding of an miRNA to an miRNA-binding site. Stability or persistence of the miRNA inhibitor will determine the length of the time that the inhibitor is effective. Loss of the miRNA inhibitor results in increased production or expression of the miRNA. In some embodiments, the miRNA inhibitors are antisense molecules. In other embodiments, the miRNA inhibitor is an antisense miRNA oligonucleotide containing 2'-OMe substitutions throughout, phosphorothioate linkages in the first two 5' and last three 3' nucleotides, and a cholesterol moiety attached at the 3' end, known as antagomirs (Krützfeldt et al., 2005).

Where the miRNA inhibitor is designed so that it directly hybridizes to the miRNA, the miRNA inhibitor must be substantially identical to the miRNA. In one embodiment, the miRNA inhibitor has at least about 70% sequence identity to the targeted miRNA. In another embodiment, the miRNA inhibitor has at least about 80% sequence identity to the targeted miRNA. In yet another embodiment, the miRNA inhibitor has at least about 90% sequence identity to the targeted miRNA. In an additional embodiment, the miRNA inhibitor has at least about 95% sequence identity to the targeted miRNA. In a further embodiment, the miRNA inhibitor has 100% sequence identity to the targeted miRNA.

The nucleic acid of the present methods can also be, or encode, an aptamer that specifically binds and inhibits a protein that inhibits wound healing. See Bunka and Stockley, 2007 and PCT Patent Publication WO08042481A2.

It is to be understood that the invention is not limited to any specific method of delivering the nucleic acid to the wound site. In most embodiments, the nucleic acid is delivered according to established procedures for providing an agent during reduced pressure therapy. For example, the reduced pressure can be provided by an apparatus that comprises a dressing, e.g., of foam or felt, that contacts the wound site. As such, in some embodiments, the nucleic acid may be bound to at least part of the plane of the dressing that is placed adjacent to the wound site. It is also contemplated that in some embodiments at least part of the miRNA or miRNA inhibitor may be bound within the dressing such that it is not placed against the wound site upon first application of the dressing adjacent to the wound site. The binding of the miRNA or miRNA inhibitor should be sufficient to be stable under conditions of binding, washing, analysis, and removal. The binding may be covalent or non-covalent. Covalent bonds may be formed directly between the nucleic acid and the dressing, or may be formed by a cross linker or by inclusion of a specific reactive group on either the solid support or the probe or both molecules. Non-covalent binding may be one or more of electrostatic, hydrophilic, and hydrophobic interactions, and covalent attachment by use of molecules such as streptavidin, and use of a combination of covalent and non-covalent interactions.

Further, the nucleic acid may be contained within a colloid, a foam, a liquid, a slurry, a suspension, a viscous gel, a paste, a putty, or other viscous material placed within the foam. The nucleic acid may also be in a colloid, foam, a liquid, a slurry, a suspension, a viscous gel, a paste, a putty, or other viscous material that is applied to the wound site at various intervals, e.g., via tubes.

The dressing is a material that is inserted substantially into or on the wound site. The dressing should be designed such that it encourages cell growth while possessing a sufficient number of open pores or channels so that wound fluids may be drained and the reduced pressure may continue unimpaired. In some embodiments, for example, the dressing comprises a cell growth lattice, matrix, or scaffold.

The dressing (e.g., foam or scaffold) may be made of any biocompatible or bioinert material such as, for example, bioresorbable polymers, non-bioresorbable polymers and fibrous growth-enhancing matrices. Suitable materials may include, but are not limited to, one or more of the following: lactide, poly(lactide) (PLA), glycolide polymers, poly(glycolic acid) (PGA), poly(lactide-co-glycolide) (PLGA), ethylene glycol/lactide copolymers, polycaprolactone, polyhydroxybutyrate, polyurethanes, polyphosphazenes, poly(ethylene glycol)-poly(lactide-co-glycolide) co-polymer, polyhydroxyacids (e.g., polyhydroxybutyrate and polyhydroxyvalerate), polycarbonates, polyamides, polyanhydrides, polyamino acids, polyortho esters, polyacetals, degradable polycyanoacrylates, polycarbonates, polyfumarates, degradable polyurethanes, proteins such as albumin, collagen, fibrin, synthetic and natural polyamino acids, polysaccharides such as alginate, heparin, and other naturally occurring biodegradable polymers of sugar units (e.g., glycosaminoglycans such as polymers of hyaluronic acid).

The dressing may be sized as to correspond to the size and shape of the wound site. As such the dressing may be cut or trimmed, or alternatively manufactured, to best fit within the wound site. When placed on a dermal wound, the wound site and dressing may be covered by a drape. A drape is a material placed over a dressing in order to form an airtight seal over the wound site when reduced pressure therapy is applied. As such, the drape should be made of a material that, given the drape shape and thickness, can maintain the reduced pressure at the wound site. Depending upon the specific needs of the wound site, the drape may be liquid tight or simply reduce the transmission of all or only certain liquids. In some embodiments, the drape should is impermeable, thus able to block or slow the transmission of either liquids or gas. In other embodiments, the drape is made of a material which permits the diffusion of water vapor but provides an air-tight enclosure. The drape will extend over the surface of the wound site and foam and extend beyond the edges of the wound. The drape is secured to the skin surface about the wound circumference by, for example, adhesive material. The foam comprises at least one reduced pressure delivery tube that is connected to the foam. Within the foam, the tubing is perforated by one or more holes. Outside of the foam, the tubing is non-perforated and extends from the foam and out from the drape.

The tubing may be made of any medical-grade tubing material, including without limitation, paralyne-coated silicone or urethane. Further, the tubing may be coated with agents to prevent the tubing adhesion to the wound. For example, the tubing may be coated with heparin, anti-coagulants, anti-fibrinogens, anti-adherents, anti-thrombinogens and/or hydrophilic substances. In some embodiments, the tubing may be used to remove wound fluids, i.e., any interstitial liquid or flowable materials located at the wound site including liquid that has exuded from the wound site tissue or its capillaries, from the wound site.

It is further contemplated that in some embodiments, the reduced pressure source may be used to control the temperature, pressure, vital gas gradients (for example, oxygen), osmotic forces, and oncotic forces. It is also contemplated that the system may further contain additional fluids containing nutrients or pharmacological agents to apply to the wound site.

In one alternate embodiment, the foam comprises a scaffold, i.e., a three dimensional porous structure used to enhance or promote the growth of cells and/or the formation of tissues. The scaffold may be infused with, coated with, or comprised of, cells, growth factors, or other nutrients that promote cell growth. The scaffold also may be used in accordance with the embodiments described herein to administer reduced pressure tissue treatment to a wound site.

Figure 1:
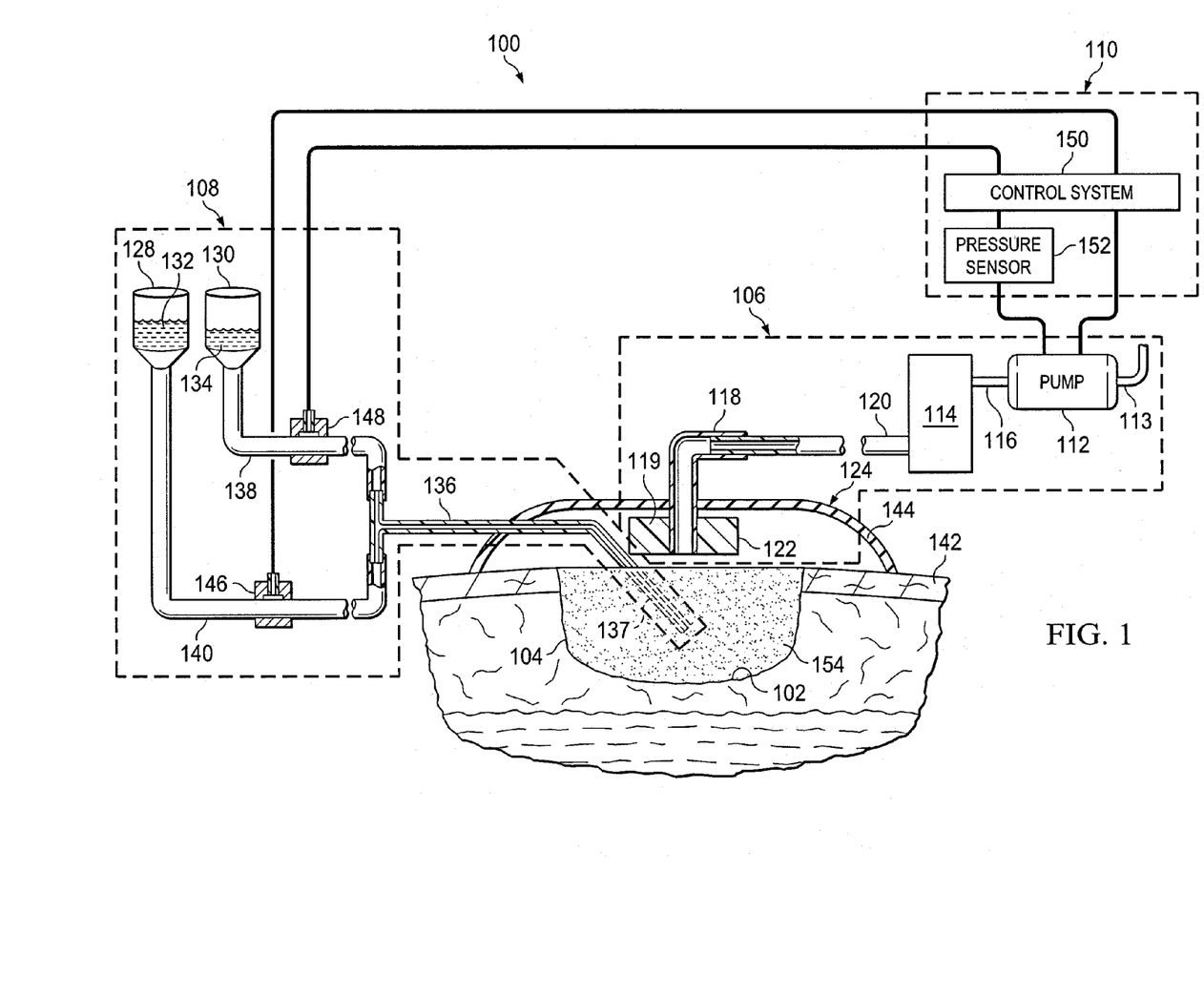
FIG. 1 is an illustration in accordance with some embodiments of the invention, showing the administration of nucleic acids or other appropriate compounds during reduced pressure therapy.

Referring to FIG. 1, a reduced-pressure treatment system 100 for providing reduced-pressure treatment to a tissue site 102, which may include a wound 104, of a patient is shown according to an illustrative embodiment. The reduced-pressure treatment system 100 includes a reduced-pressure subsystem 106, a fluid supply subsystem 108, and a controller 110.

The reduced-pressure subsystem 106 supplies reduced pressure to the tissue site 102, and includes a reduced-pressure source 112 that provides reduced pressure. The reduced-pressure source 112 may be any device for supplying a reduced pressure, such as a vacuum pump, wall suction, or other source. While the amount and nature of reduced pressure applied to the tissue site 102 will typically vary according to the application, the reduced pressure will typically be between −5 mm Hg and −500 mm Hg and more typically between −100 mm Hg and −300 mm Hg. The reduced-pressure source 112 includes an exhaust port 113 for the release of gas during operation of the reduced-pressure source 112.

The reduced-pressure source 112 is fluidly coupled to a canister 114, or reservoir, via conduit 116. The canister 114 is fluidly coupled to a protruding portion 118 of a reduced-pressure connecting member 119 via conduit 120. The canister 114 receives exudates or other fluids that are drawn from the wound 102 as a result of the reduced pressure applied by the reduced-pressure subsystem 106. A filter or other device may be disposed at or near the canister 114, such as at the junction between the canister 114 and the conduit 116, to prevent exudate or other fluid from entering the reduced-pressure source 112.

A portion 122 of the reduced-pressure connecting member 119 that is adjacent the tissue site 102 is covered by a drape 124. The drape 124 helps to seal the tissue site 102 so that a therapeutic reduced pressure can be applied and maintained at the tissue site 102. The drape 124 may be any material that provides a pneumatic seal. The drape 124 may, for example, be an impermeable or semi-permeable, elastomeric material that has pore sizes less than about 20 microns. "Elastomeric" means having the properties of an elastomer. It generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of drape materials include a silicone drape, 3M Tegaderm® drape, acrylic drape such as one available from Avery Dennison, or an incise drape.

An adhesive may be used to hold the drape 124 against the patient's epidermis 142 or another layer, such as a gasket or additional sealing member. The adhesive may take numerous forms. For example, the adhesive may be a medically acceptable, pressure-sensitive adhesive that extends about a periphery 144 of the drape 124.

The fluid supply subsystem 108 supplies fluid to the tissue 102, and includes at least two reservoirs 128 and 130. The first reservoir 128 holds a nucleic acid-containing fluid 132, and the second reservoir 130 includes a fluid 134. The fluid 134 in the second reservoir 130 may also include a nucleic acid, in which case the nucleic acid may be different from that contained in the nucleic acid-containing fluid 132 in the first reservoir 128. In another embodiment, the fluid supply subsystem 108 may include only one reservoir. The first and second reservoirs 128, 130 are fluidly coupled to a fluid supply conduit 136 via secondary fluid supply conduits 138 and 140, respectively. The fluid supply conduit 136 may be perforated at the distal portion 137 to facilitate the release of fluid at the tissue site 102.

The fluid supply subsystem 108 also includes a first valve 146 and a second valve 148. The first and second valves 146, 148 are capable of opening and closing to allow or prevent the flow of fluid 132, 134 from the first and second reservoirs 128, 130 through the secondary fluid supply conduits 138, 140, respectively.

Controller 110 includes a control system 150 and a pressure sensor 152, and controls the operation of the reduced-pressure subsystem 106 and the fluid supply subsystem 108. Regarding the reduced-pressure subsystem 106, the controller 110 can direct the reduced-pressure source 112 to apply a variable or a non-variable reduced pressure over time. When applying the a variable reduced pressure, the controller 110 can measure the pressure at the reduced-pressure source 112 or the tissue site 102 using the pressure sensor 152. The pressure measured by the pressure sensor 152 can then be used by the control system 150 to control the reduced pressure applied by the reduced-pressure source 112. For example, the control system 150 can increase or decrease the reduced pressure applied by the reduced-pressure source 112 to ensure that a therapeutic reduced pressure is maintained at the tissue site 102. The control system 150 can also oscillate the reduced pressure applied by the reduced-pressure source 112 and determine the optimum drive frequency based on the pressure detected by the pressure sensor 152.

The controller 110 also controls the release of the fluids, including the fluids 132, 134 in the first and second reservoirs 128, 130, into the tissue site 102 using the first and second valves 146, 148. For example, the controller 110 can direct both of the valves 146, 148 to be open or closed, or can direct only one of the valves 146, 148 to be open while the other is closed.

The controller 110 can also coordinate the operations of the reduced-pressure subsystem 106 and the fluid supply subsystem 108. For example, the controller 150 may alternate between the application of reduced pressure by the reduced-pressure subsystem 106 and fluid by the fluid supply subsystem 108. By alternating between the application of reduced pressure and fluid, the fluid, including any nucleic acid, is allowed to perform a therapeutic function, including those described in the illustrative embodiments, before being drawn into the canister 114 by the application of reduced pressure. The controller 110 is also able to apply both reduced pressure and fluid simultaneously. In one embodiment, the fluid in one or both of the reservoirs is motivated toward the tissue site 102 using the reduced pressure generated by the reduced-pressure source 112 and maintained at the tissue site 102. In other examples, the fluid from the fluid supply subsystem 108 may also be motivated toward the tissue site 102 using gravity or a pump.

A manifold 154 is insertable, and, in some cases, conformable, into the tissue site 102 to distribute the reduced pressure or fluid that is applied to the tissue site 102. The manifold 154 is a substance or structure that is provided to assist in applying reduced pressure to, delivering fluids to, or removing fluids from the tissue site 102. The manifold 154 typically includes a plurality of flow channels or pathways that are interconnected to improve distribution of fluids provided to and removed from the tissue site 102 around the manifold 154. The manifold 154 may be a biocompatible material that is capable of being placed in contact with tissue site 102 and distributing reduced pressure to the tissue site 102. Examples of manifolds 154 may include, for example, without limitation, devices that have structural elements arranged to form flow channels, such as, for example, cellular foam, open-cell foam, porous tissue collections, liquids, gels, and foams that include, or cure to include, flow channels. The manifold 154 may be porous and may be made from foam, gauze, felted mat, or any other material suited to a particular biological application. In one embodiment, the manifold 154 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. Other embodiments might include "closed cells." These closed-cell portions of the manifold may contain a plurality of cells, the majority of which are not fluidly connected to adjacent cells. The closed cells may be selectively disposed in the manifold 154 to prevent transmission of fluids through perimeter surfaces of the manifold 154. In some situations, the manifold 154 may also be used to distribute fluids such as medications, antibacterials, growth factors, and various solutions to the tissue site 102. Other layers may be included in or on the manifold 154, such as absorptive materials, wicking materials, hydrophobic materials, and hydrophilic materials.

Different wound conditions may require different dosage regimens and formulations of the nucleic acid. The practitioner may determine what exact nucleic acids go into the treatment formulation, the treatment regimen, i.e., dosage and schedule of treatment. These parameters will often depend upon the practitioner's experience with wound healing.

It is also contemplated that in some embodiments the nucleic acids used would depend upon the expression of RNA or miRNA nucleic acid sequences at the wound site of a specific patient. The level of RNA or miRNA expression can be determined by whatever means are convenient to one skilled in the art.

Further, the practitioner may also use other therapeutics with the miRNA or miRNA inhibitor treatment. For example, the practitioner may use various drugs that bind to the receptors of which modulates expression or activity of a nucleic acid related to wound healing. The practitioner may also treat the wound with additional factors that increase endothelial growth and proliferation such as, for example, lactic acid. The practitioner may also include other therapeutic treatments that increase wound healing, such as, for example, use of nitric oxide at the wound to stimulate keratinocyte migration. The practitioner may also add protective agents to the wound such as antibiotics.

The application is also directed to a system for treating a wound site. The system comprises a distribution manifold; a reduced pressure source fluidly connected to said distribution manifold to deliver reduced pressure to the wound site; and a nucleic acid source fluidly connected to said distribution manifold to deliver nucleic acid to the wound site sufficient to treat the wound.

In some embodiments of this system, the nucleic acid encodes a protein. Where the nucleic acid encodes a protein, the nucleic acid can be operably linked to a control element, e.g., a promoter, enhancer, etc., that directs expression of the protein when the nucleic acid is inside a cell in the wound.

In some aspects, the nucleic acid encodes a structural protein, for example a collagen, a fibronectin, an elastin or a laminin. In other aspects, the nucleic acid encodes an enzyme, for example a Tie-1, a Tie-2, a c-kit, or an HIF-1α.

The nucleic acid can alternatively encode a cytokine. Non-limiting examples include a fibroblast growth factor (FGF), a vascular endothelial growth factor (VEGF), a platelet derived growth factor (PDGF), a transforming growth factor-β (TGFβ), a TGFα, a stem cell factor (SCF), an angiopoietin 1 (Ang1), an epidermal growth factor (EGF), an interleukin, an insulin-like growth factor (IGF), a laminin, a hepatocyte growth factor (HGF), an adrenomedullin, a keratinocyte growth factor (KGF), a bone morphogenic protein (BMP), a cartilage derived morphogenic protein (CDMP), and a placental growth factor (PlGF). In some aspects, the cytokine is angiogenic. Examples of angiogenic cytokines are bFGF, VEGF-A, TGF-β, SCF, Ang1, laminin-8, HGF, adrenomedullin, and PlGF.

The nucleic acid of this system can also encode an enzyme inhibitor. An example of a useful enzyme inhibitor here is a tissue inhibitor of metalloproteinase.

Further, the nucleic acid can encode a cell surface receptor, for example an integrin. Also, the nucleic acid can encode a transcription factor, for example a HoxD3, a hypoxia-inducible factor-1α (HIF-1α), or a Net.

The nucleic acid can also encode a protein that increases expression in response to reduced pressure treatment of the wound site. Examples include interleukin 6 (IL-6), chemokine ligand 7 (Ccl7), tissue inhibitor of metalloproteinase 1 (TIMP1), integrin alpha M (Itgam), suppressor of cytokine signaling 3 (Socs3), matrix metalloproteinase-8 (MMP-8), macrophage inflammatory protein-1 alpha receptor gene (MIP1R), toll like receptor 1 (TLR1), tumor necrosis factor receptor superfamily member 1b (Tnfrsf1b), heat shock protein 70 (Hsp70), calmodulin-like 3, and keratin complex 1 acidic gene 14 (Krt1-14), which were identified in the work described in the Example In other embodiments of this system, the nucleic acid specifically inhibits expression of a protein that inhibits wound healing. Non-limiting examples of proteins that inhibit wound healing are small mothers against decapentaplegic homolog 3 (Smad3), vascular endothelial growth factor receptor 1 (VEGFR1), VEGFR2, VEGFR3, connexin, and myostatin.

Where the nucleic acid inhibits expression of a protein that inhibits wound healing, the nucleic acid can be an antisense nucleic acid specific to an mRNA encoding the protein. Alternatively, the nucleic acid can be a ribozyme specific to an mRNA encoding the protein, or an miRNA specific to an mRNA encoding the protein.

The nucleic acid of the system can also inhibit a naturally occurring miRNA that inhibits wound healing. Here, for example, the naturally occurring miRNA can inhibit expression of VEGF.

The nucleic acid of the system can also be an aptamer that specifically binds and inhibits the protein that inhibits wound healing.

As with the methods described above, the nucleic acid of this system can be part of any appropriate vector. Preferred vectors include viral vectors and plasmids. This application is also directed to the use of reduced pressure and a nucleic acid that promotes wound healing for treatment of a wound site. Additionally, the application is directed to the use of a nucleic acid that promotes wound healing for the manufacture of a medicament for treating a wound site that is undergoing reduced pressure treatment.

EXAMPLE

Comparative Analysis of Global Gene Expression Profiles Between Diabetic Rat Wounds Treated with Vacuum Assisted Closures® Therapy, Moist Wound Healing or Gauze Under Suction Example Summary How differential gene expression affects wound healing is not well understood. In this study, the Zucker Diabetic Fatty (fa/fa) male inbred rat was used to investigate gene expression during wound healing in an impaired wound healing model. Whole genome microarray surveys were used to gain insight into the biological pathways and healing processes in acute excisional wounds treated with V.A.C.® Therapy, moist wound healing or gauze under suction. Global gene expression analyses after two days of healing indicated major differences with respect to both number of genes showing changes and pathway regulation between the three different wound treatments. Statistical analysis of expression profiles indicated that 5072 genes showed a greater than 1.6 fold change with V.A.C.® Therapy compared to 3601 genes with moist wound healing, and 3952 genes with gauze under suction. Pathways and related genes associated with the early phases of wound healing diverged between treatment groups. For example, pathways such as inflammation, angiogenesis, and cytoskeletal regulation were associated with over expressed gene expression following V.A.C.® Therapy. This study is the first to assess wound healing via whole genome interrogation in a diabetic rat model treated with different healing modalities.

Introduction

Diabetes affects 246 million people worldwide and is expected to impact 380 million by 2025 (IDF, 2005a). In the United States alone, over 20.8 million people are known to have diabetes (American Diabetes Association, 2007) and it is one of the most common causes of non-traumatic lower extremity amputations due to non-healing wound complications in Europe and the United States (Jeffcoate, 2005; Medina et al., 2005; IDF, 2005b). In 2002, about 82,000 non-traumatic, lower-limb amputations were performed on U.S. diabetic patients secondary to wound complications due to impaired sensation and infection (Centers for Disease Control, 2005). Foot ulceration is generally associated with peripheral neuropathy and develops in about 15% of patients with diabetes (Medina et al., 2005; Brem et al., 2006; Andros et al., 2006). Since diabetic wounds are complex, proper wound bed preparation and early intervention is essential to successful healing (Sharman, 2003). Research indicates that 67% of diabetic foot ulcers are unhealed after 20 weeks of care using standard wound healing methods (Searle et al., 2005). Vacuum Assisted Closure® Therapy is widely used in the treatment of diabetic foot ulcers and has been clinically proven to prepare the wound bed for closure in both acute and chronic wounds (Brem et al., 2006; Andros et al., 2006; Armstrong et al., 2005; Venturi et al., 2006; Argenta and Morykwas, 1997). Gene signature changes during V.A.C.® Therapy are unknown and a "wound healing gene signature" has yet to be defined.

Wound healing may be classified into four overlapping phases: hemostasis, inflammation, proliferation and remodeling (Diegelmann and Evans, 2004). Hemostasis starts at the moment the tissue is injured and when blood moves into the site of injury. The inflammation phase follows hemostasis whereby neutrophils and macrophages appear initiating the phagocytotic processes with increased secretion of growth factors and inflammatory cytokines, including tumor necrosis factor alpha (TNF-α) and interleukin 6 (Diegelmann and Evans, 2004; Schultz et al., 2005; Stadelmann et al., 1998). Neutrophils also may help to activate fibroblasts and epithelial cells (Schultz et al., 2005; Li et al., 2003). During the proliferation phase, fibroblasts migrate into the wound. They deposit new extracellular matrix, stimulate protease inhibitor activity, promote angiogenesis, and release cytokines such as interleukins, fibroblast growth factor, and TNF-α. In the remodeling phase, the wound becomes re-epithelized, the extracellular matrix becomes cross-linked, and the healed wound becomes less vascular.

Microarray studies during the various phases of wound healing may provide insight into gene expression patterns leading to the various events of the wound healing cascade. Of interest are the early steps in wound healing such as the inflammatory phase given that quick resolution will result in healing, whereas a delay or inability to resolve the inflammatory response could lead to chronic ulceration as seen in diabetic patients (Schultz et al., 2005). Chronic wounds with prolonged or non-resolving inflammation phases are associated with increased levels of proteases such as matrix metallopeptidases which destroy components of the extracellular matrix and damage growth factors and receptors needed for healing (Id.). Assessing trends in resolution of the inflammatory phase by way of up or down regulation of particular genes could lead to the creation of improved treatment modalities.

This study used whole genome survey microarrays and TaqMan® quantitative real-time PCR technologies to track changes in gene expression profiles during the early phase of healing in Zucker Diabetic Fatty (ZDF) rats. It compares gene expression over the first two days of healing using two different negative pressure wound therapy modalities and moist wound healing as a control. The 48 hour time point was chosen to examine gene expression as representative of the first dressing change during V.A.C.® Therapy. This is the first study to interrogate the entire genome by assessing differential gene expression during the early phase of wound healing using three different wound treatment modalities: V.A.C.® Therapy (V.A.C.®), moist wound healing (MWH), or gauze under suction (GUS).

Methods

Animals.

Male ZDF rats were obtained from Charles River Laboratories (Wilmington, Mass.) at 17-22 weeks of age. Male rats in this inbred strain develop noninsulin-dependent type 2 diabetes and are characterized by impaired wound healing (Clark et al., 1983). Blood glucose levels were monitored using a glucometer (LifeScan, Inc./Johnson & Johnson, Milpitas, Calif.) to verify the animals were diabetic (glucose levels 339 mg/dL→600 mg/dL). Animals were housed individually, maintained at 22-24° C. with a 12 h light/dark cycle, and allowed food and water ad libitum. All animal experiments were approved by the University of Texas Health Science Center Institutional Animal Use and Care Committee. Six animals were treated with V.A.C.® Therapy (V.A.C.®), six animals were treated with Tegaderm™ (MWH), and four animals were treated with gauze under suction (GUS).

Wound Creation and Area.

The day of wound creation was designated day 0. The hair on the dorso-lateral back was removed and one circular 3 cm diameter full thickness wound was created on the mid-dorsum of each animal. Wound area was calculated using the Visitrak grid system (Smith & Nephew, Inc. Largo, Fla.) at wound creation and end of treatment on day 2.

Treatment of Wounds.

Wounds treated with V.A.C.® Therapy were fitted with a polyurethane dressing (V.A.C.® GranuFoam® Dressing, KCI, San Antonio, Tex.), and covered with a polyurethane drape (V.A.C.® Drape, KCI) and a connector tubing (T.R.A.C.® Pad, KCI). The proximal end of the tubing was connected to a swivel mounted on the top of the cage to allow the animals' free mobility and access to food and water. The swivel was in turn connected to a V.A.C.® Therapy ATS® System (KCI) set to deliver continuous subatmospheric pressure of −125 mmHg, the common clinical setting.

MWH treated wounds received Tegaderm™ Transparent Film Dressing (3M Health Care, St. Paul, Minn.). This dressing was used as a baseline, untreated control. The same style of connector tubing was placed on top of the MWH dressing so that all animals received a comparable tethering device. This was done to control for stress to the back of the animals due to the added weight of the tethering device.

For GUS, 3×3 inch Aquaphor™ Gauze (Smith & Nephew, Inc.) was cut to 3 cm diameter and placed directly in the wound bed. The tip of a Jackson-Pratt™ (Cardinal Health, Dublin, Ohio) drain was trimmed and the end was placed in the wound over the Aquaphor™. A piece of double sided adhesive hydrogel was applied to the periwound tissue to anchor the drain and to keep the dressing assembly from repositioning. The drain was covered with approximately 4 layers of sterile gauze and then covered with an Opsite™ (Smith & Nephew, Inc.) dressing to create a seal. The dressing assembly was connected to a swivel as previously mentioned and the swivel was connected to a Versatile 1™ pump (BlueSky, Carlsbad, Calif.). The pump was set at continuous suction of −75 mmHg, the common clinical setting used for this therapy, and a handheld manometer (Omega, Stamford, Conn.) was used to monitor Versatile 1™ pressure.

To control pain, all animals received approximately 0.04 mg/kg buprenorphine twice daily as determined by the attending veterinarian during the first 24-48 hours post wounding. After all experiments were completed, rats were euthanatized by exsanguination.

Tissue Samples.

On the day of wound creation, a portion of the non-wounded skin was quickly placed into RNAlater® (Ambion, Austin, Tex.) and stored at −20° C. for subsequent preparation of total RNA. At the conclusion of the experiment on day 2, wounded tissue was quickly removed and stored in RNAlater® at −20° C. Total RNA was isolated from tissue using TRIzol® (Invitrogen, Carlsbad, Calif.) with modifications to remove DNA using RNeasy columns and a DNase I Kit (Qiagen, Valencia, Calif.). RNA was stored at −80° C. in nuclease-free $H_2O$ (Qiagen). Quality and quantity of RNA was determined using an Experion Automated Electrophoresis system (Bio-Rad, Hercules, Calif.) and the same samples were divided into aliquots for microarray and TaqMan® quantitative real-time PCR analysis (Applied Biosystems, Foster City, Calif.).

Microarray.

In this study, data from six biological replicates for V.A.C.® and MWH and four biological replicates for GUS for a total of 32 microarrays were compared. Gene expression profiles were generated using the Applied Biosystems Rat Genome Survey Microarray. Each microarray contains approximately 28,000 features that include a set of about 1,000 controls. Each microarray uses 26,857 60-mer oligonucleotide probes designed against 27,088 genes covering 43,508 transcripts.

Nucleic acid labeling and raw microarray data generation were carried out at the Vanderbilt Microarray Shared Resource. Prior to amplification and labeling, the quality and quantity of total RNA isolated from tissues was determined using the Agilent 2100 Bioanalyzer (Agilent Technologies, Santa Clara, Calif.). Briefly, 750 ng of total RNA was used to transcribe DIG-labeled cRNA using the Applied Biosystems NanoAmp™ RT-IVT Kit. Ten micrograms of DIG-labeled cRNA was hybridized onto the rat microarrays. Microarray processing, chemiluminescence detection, imaging, auto gridding, and image analysis were performed according to manufacturer's protocols and the AB1700 Chemiluminescent Microarray Analyzer Software v. 1.0.3. Raw data were analyzed using the ABarray data analysis package (bioconductor.org). Probe signal intensities across microarrays were normalized using the quantile method (Bolstad et al, 2003). Features with signal/noise values >3 and quality flag values <5,000 were considered detected and were compared by t-test using a fold change >1.6, a Benjamini and Hochberg False Discovery Rate (FDR) of <0.05 (Benjamini and Hochberg, 1993), and/or a p-value of <0.05. Lists of differentially expressed genes were then classified using the PANTHER™ database (Thomas et al., 2003; 2006). Fold change values were calculated by dividing day 2 (wound) values by day zero (unwounded) values.

Validation Using TagMan®-Based Quantitative Real-Time PCR Gene Expression Assays.

Validation of the microarray data was performed by quantitative real-time PCR. Approximately 1 μg of total RNA of each sample per 100 μl reaction was used to generate cDNA using the High Capacity cDNA Reverse Transcription Kit (Applied Biosystems). The TaqMan® assays for the FAM™ labeled gene of interest was duplexed with the VICE labeled 18S RNA endogenous control assay using a 7500 Fast real-time PCR system (Applied Biosystems). For each sample, three technical replicates per gene were run in a 96-well format plate. On each plate, a no-template-control was also run in triplicate. Relative quantification analysis was performed using SDS software v. 1.3.1 (Applied Biosystems).

Results

Global Gene Expression.

Microarray-generated global gene expression profiles detected an average of 14,559 probes in V.A.C.® treated samples. This compares to averages of 14,543 and 13,681 probes in MWH and GUS respectively. Genes based on expression levels (1.0-4.0 fold change) demonstrated that expression levels within a treatment group are consistent; gene expression levels for V.A.C.® samples group together tightly and this was also observed in the other treatment groups as well using quantile normalized expression and hierarchical clustering (data not shown). Using a p value cut off of ≤0.05, 5072 genes were found to be differentially expressed (either up or down regulated) with a fold change greater than or equal to 1.6 over the two day treatment with V.A.C.® Therapy (Table 1). In comparison, 3601 genes were significantly differentially expressed for wounds treated with MWH and 3952 genes were significantly differentially expressed in wounds treated with GUS.

There were approximately 28% and 41% more genes up and downregulated following V.A.C.® than GUS treatment and MWH treatment, respectively. Of the 2857 upregulated genes during the first 2 days of V.A.C.® Therapy, 479 were upregulated more than 2 times for V.A.C.® above GUS treatment and 249 were upregulated more than 2 times for V.A.C.® above MWH treatment. Conversely, of the 2342 genes upregulated following GUS treatment, only 13 were upregulated more than 2 times following GUS than following V.A.C.®. Of the 2053 genes upregulated during moist wound healing only 14 were upregulated more than 2 times following MWH than following V.A.C.®.

TABLE 1

Table 1: Number of genes up (↑) and down (↓) regulated (p < 0.05) in the three wound healing treatment groups based on fold change (FC).

| V.A.C. ® | | MWH | | GUS | |
| --- | --- | --- | --- | --- | --- |
| ↓ FC | # of genes | ↓ FC | # of genes | ↓ FC | # of genes |
| 1.6-10 | 1707 | 1.6-10 | 1176 | 1.6-10 | 1184 |
| 10-50 | 358 | 10-50 | 251 | 10-50 | 271 |
| 50-100 | 72 | 50-100 | 57 | 50-100 | 60 |
| >100 | 78 | >100 | 64 | >100 | 95 |
| Total | 2215 | Total | 1548 | Total | 1610 |

TABLE 1-continued

Table 1: Number of genes up (↑) and down (↓) regulated (p < 0.05) in the three wound healing treatment groups based on fold change (FC).

| V.A.C. ® | | MWH | | GUS | |
|---|---|---|---|---|---|
| ↑ FC | # of genes | ↑ FC | # of genes | ↑ FC | # of genes |
| 1.6-10 | 2683 | 1.6-10 | 1988 | 1.6-10 | 2334 |
| 10-50 | 163 | 10-50 | 62 | 10-50 | 8 |
| 50-100 | 9 | 50-100 | 1 | 50-100 | 0 |
| >100 | 2 | >100 | 2 | >100 | 0 |
| Total | 2857 | Total | 2053 | Total | 2342 |
| Grand Total | 5072 | | 3601 | | 3952 |

PANTHER™ was used to classify the pathways represented by the aforementioned genes. Genes in the following pathways were found to be significantly over represented in all three treatment groups, with V.A.C.® having the most genes showing differential expression (summarized in Table 2): Inflammation mediated by chemokine and cytokine signaling (V.A.C.® 224 genes, MWH 176 genes, GUS 213 genes); integrin signaling (V.A.C.® 177, MWH 125, GUS 155); B cell activation (V.A.C.® 62, MWH 47, GUS 52); interleukin signaling (V.A.C.® 100, MWH 68, GUS 77); PDGF signaling (V.A.C.® 129, MWH 90, GUS 92); Cytoskeletal regulation by Rho GTPase (V.A.C.® 82, MWH 58, GUS 70); and angiogenesis (V.A.C.® 153, MWH 111, GUS 120). There were also pathways where one or more treatment groups, either MWH or GUS, were not associated with significant gene over representation. Those included pathways of oxidative stress response (V.A.C.® 49, MWH (not significant), GUS 38); G-protein signaling (V.A.C.® 90, MWH 69, GUS (not significant); VEGF signaling (V.A.C.® 53, MWH (not significant) GUS 48); FGF signaling (V.A.C.® 74, MWH (not significant), GUS 59); pentose phosphate pathway (V.A.C.® 16, MWH (not significant), GUS (not significant); and apoptosis signaling (V.A.C.® 85, MWH (not significant), GUS 72).

TABLE 2

| | Number of genes (obs/exp) | | |
|---|---|---|---|
| Pathways of Upregulated Genes | V.A.C. ® | MWH | GUS |
| Inflammation mediated by chemokine and cytokine signaling pathway | 244/105 | 176/75 | 213/82 |
| Integrin signaling pathway | 177/76 | 125/55 | 155/60 |
| Angiogenesis | 153/79 | 111/57 | 120/62 |
| PDGF signaling pathway | 129/62 | 90/45 | 92/49 |
| Interleukin signaling pathway | 100/57 | 68/41 | 77/44 |
| G-Protein signaling | 90/61 | 69/44 | 72/47[#] |
| Apoptosis signaling | 85/50 | 54/36[#] | 72/39 |
| Cytoskeletal regulation by Rho GTPase | 82/37 | 58/27 | 70/29 |
| FGF signaling | 74/46 | 53/33[#] | 59/36 |
| B cell activation | 62/30 | 47/22 | 52/24 |
| VEGF signaling | 53/28 | 35/20[#] | 48/22 |
| Oxidative stress response | 49/25 | 31/18[#] | 38/19 |
| Pentose phosphate pathway | 16/5 | 12/4[#] | 12/4[#] |

Table 2: Thirteen pathways of interest to wound healing expressed as number of genes observed over genes expected (obs/exp) in PANTHER ™ and showing significant gene over representation following two days of treatment with either V.A.C. ® Therapy (V.A.C. ®), moist wound healing (MWH), or gauze under suction (GUS). Pathways with fold change greater or equal to 1.6 and p values ≤0.05 were used for analysis. Ratios which were not statistically significant (p > 0.05) are represented by number sign ([#]).

Since V.A.C.® treatment improved and accelerated wound healing, genes involved in the above pathways that have increased expression under V.A.C.® would be expected to benefit from transfection and expression of genes in those pathways into cells in the wound tissue.

Twelve genes of interest, based upon high fold change and including representatives from the over-represented pathways previously mentioned, were examined more closely for potential development of wound healing signatures. These genes along with the signaling pathway represented and associated fold change are presented in Table 3. There is a higher fold change for the majority of the genes in the V.A.C.® Therapy group of both upregulated and downregulated genes than in the other two treatment groups.

TABLE 3

Table 3: Fold changes for the genes was calculated for each treatment group form microarray (denoted by the M after the treatment group) and quantitative real-time PCR data (denoted by the q after the treatment group).

| | | Fold Change | | | | | |
|---|---|---|---|---|---|---|---|
| Gene Name | Signaling Pathway | V.A.C. ® M | V.A.C. ® q | MWH M | MWH q | GUS M | GUS q |
| interleukin 6 | Cytokine signaling/Interleukin signaling | 80.8 | 478.9 | 29.8 | 208.1 | 7.9 | 28.6 |
| chemokine (C-C motif) ligand 7 | Cytokine signaling | 50.3 | 127.3 | 16.0 | 66.5 | 6.7 | 15.6 |
| tissue inhibitor of metalloproteinase 1 | Metalloprotease inhibitor/proteolysis | 39.3 | 159.9 | 35.8 | 170.5 | 5.1 | 31.1 |
| integrin alpha M | Integrin signaling | 25.5 | 18.9 | 14.8 | 14.3 | 5.4 | 6.1 |
| suppressor of cytokine signaling 3 | Inflammation/Interferon gamma signaling | 24.6 | 31.0 | 11.1 | 11.7 | 5.9 | 8.6 |
| matrix metalopeptidase 8 | Plasminogen activating cascade | 18.5 | 131.0 | 4.2 | 44.5 | 7.6 | 22.8 |
| macrophage inflammatory protein-1 alpha receptor gene | Inflammation | 15.2 | 34.0 | 6.2 | 19.5 | 3.8 | 7.9 |
| toll-like receptor 2 | Toll receptor pathway | 15.1 | 63.8 | 4.1 | 37.1 | 5.4 | 13.0 |
| tumor necrosis factor receptor superfamily, member 1b | Cytokine/Immunity and defense | 14.4 | 14.2 | 6.1 | 9.7 | 3.6 | 6.6 |
| heat shock protein 70 | Apoptosis signaling pathway | 2.9 | 6.5 | 2.6 | 5.5 | 1.8 | 4.8 |
| calmodulin-like 3 | G-protein signaling | −208.8 | −662.9 | −126.9 | −292.9 | −38.1 | −1265.2 |
| keratin complex 1, acidic, gene 14 | Intermediate filament/Cell structure | −707.9 | −6652.6 | −314.4 | −6716.1 | −14.3 | −17.8 |

Ten upregulated and two downregulated genes (denoted by negative numbers) are shown. Genes were selected based on either high fold change or fold changes in one treatment group which were at least 2 times higher than for other treatment groups. Differentially expressed genes with a p < 0.05 were considered significant.

Global Gene Relationships.

Figure 2:
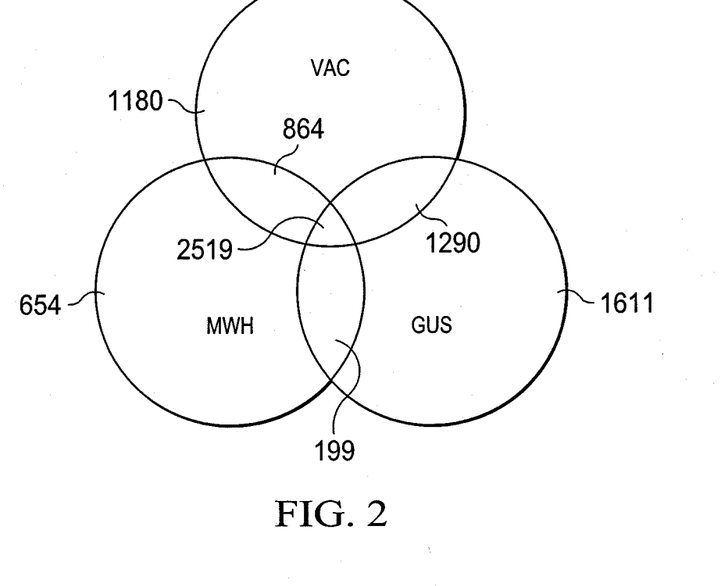
FIG. 2 is a Venn diagram of overlapping lists ($p<0.05$) of genes whose expression during wound healing was altered by V.A.C.® Therapy (V.A.C.®), moist wound healing (MWH), and gauze under suction (GUS).

When genes were evaluated for unique expressors, it was found that V.A.C.® was associated with differential expression of 1180 unique genes not expressed in other treatment groups; 654 genes were unique to MWH and 1611 genes were unique to GUS (p<0.05) (FIG. 2). Analysis of relationships between groups for common expressors showed that 864 genes were common to both V.A.C.® and MWH treated wounds, 199 genes were common to both MWH and GUS treated wounds, and 1290 genes were common to both V.A.C.® and GUS treated wounds. There were also 2519 genes found to be 'common wound healing gene signatures' since these genes were common between all three treatment groups.

Validation of Microarray Results.

Microarray results were validated by quantitative real-time PCR analysis of 27 individual genes. These genes were chosen by placing genes into a matrix to best represent all combinations in fold change bins from low (1.0-1.2), medium (1.2-4) and high (>4) and in expression levels from low, medium and high.

There was a 90% correlation between microarray and quantitative real-time PCR results. This percentage may be somewhat low due to the fact that certain selected TaqMan® inventoried gene assays might not have covered all possible gene transcripts for the gene of interest.

Wound Healing Phenotype.

Figure 3:
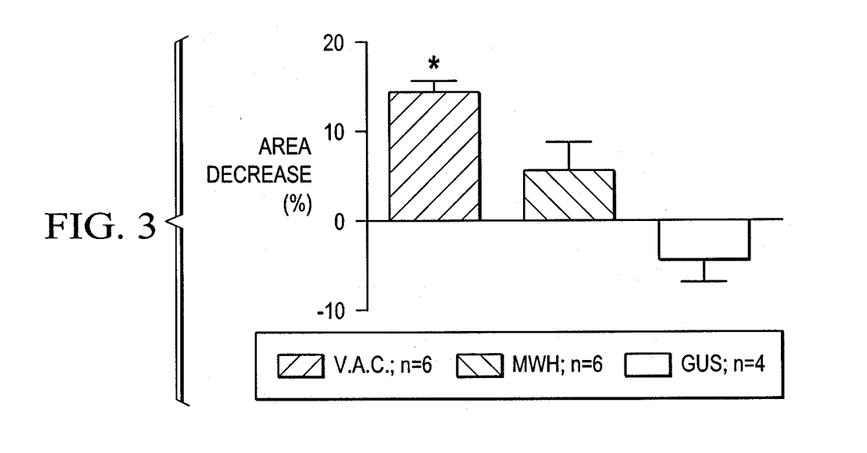
FIG. 3 is a graph showing wound area measurements between the three different wound healing modalities of V.A.C.® Therapy (V.A.C.®), moist wound healing (MWH), and gauze under suction (GUS). Values are expressed as Mean±SEM. Percent change represents the average closure rate±standard deviation. V.A.C.® had significantly greater decrease in wound area than the other two modalities; whereas GUS caused an increase in wound area. V.A.C.® was statistically significant ($p<0.05$) over MWH and GUS as represented by the asterisk (*).

Wound areas were measured on all animals over the first two days of healing. V.A.C.® treated animals had a significantly higher percentage wound closure than did the other treatment groups (p<0.05; FIG. 3). The percent change shown in FIG. 3 represents the average closure rate±standard deviation. V.A.C.® had significantly greater decrease in wound area than the other two modalities; whereas GUS caused an increase in wound area. V.A.C.® was statistically significant (p<0.05) over MWH and GUS as represented by the asterisk (*). Means of percentage wound closure over the first 2 days of treatment were V.A.C.® 14.0±1.6%, MWH 5.4±3.5%, and GUS −4.3±2.6%. The GUS group wounds showed no significant closure during the first 2 days of therapy; on the contrary, wound sizes increased from day zero to day 2, which is believed to be a direct effect of the therapy in this model.

Discussion

Pathways.

Analyzing gene expression patterns are crucial to understanding the biology of wound healing, especially in the very early stages where it is not clearly understood why some wounds heal while others become chronic. In the current study, the impact of three treatment modalities (V.A.C.®, MWH, and GUS) on gene expression during the early phases of wound healing in diabetic ZDF rats was assessed. The analysis showed that a substantial number of genes were differentially expressed over the first two days of healing with V.A.C.® Therapy. Differentially expressed genes following V.A.C.® mapped to pathways differently than for the other two modalities tested. Indeed, there were more pathways with significantly over represented gene numbers following V.A.C.® Therapy than for GUS or MWH.

Overrepresentation of differentially expressed genes in pathways indicates that the treatment is having a specific effect on certain pathways rather than arbitrarily affecting all pathways in the same manner. The over represented pathways are of known importance to wound healing. For example, inflammation, the second phase of wound healing, is characterized initially by the infiltration of neutrophils and later by macrophage phagocytosis of neutrophils (Meszaros et al., 2000) and the release of platelet derived growth factor (PDGF). PDGF, along with other factors, leads the wound from the inflammation phase and into the proliferation phase of wound healing (Goldman, 2004; Harding et al., 2002). As shown in Table 2, V.A.C.® Therapy resulted in a significant over representation (both up and down regulated genes) of the inflammation pathway. This included inflammation mediated by chemokine and cytokine signaling pathway, interleukin signaling, and PDGF signaling. Interleukins are a class of cytokines and are important in the early stages of inflammation. While inflammation is necessary for proper wound healing, resolution of the inflammatory response in a timely manner is important to successful healing. Failure to resolve inflammation in a timely fashion is associated with wound chronicity (Sibbald et al., 2003). The inflammation pathway genes over represented included both inflammatory and anti-inflammatory genes. For example, suppressor of cytokine signaling 3 and 4, and IL-10 which modulate inflammation were all upregulated.

The third, or proliferative, phase of wound healing typically occurs from day 1 to day 30 and often peaks at day three following wounding in humans and is characterized by the migration of fibroblasts into the wound (Diegelmann and Evans, 2004). Once in the wound, fibroblasts proliferate and are also involved in the production of extracellular matrix to help fill the wound with granulation tissue (Id.). Cell movement, including migration, is associated with several different pathways including Rho GTPase and integrin mediated pathways. In tissues treated with V.A.C.® Therapy for 2 days, the cytoskeletal regulation by Rho GTPase pathway was significantly over represented. V.A.C.® treated wounds differentially expressed 82 genes, MWH treated wounds differentially expressed 58 genes, and GUS treated wounds differentially expressed 70 genes. This pathway affects cytoskeletal elements such as actin and microtubules which enable cells to move and change shape. Also important during the proliferative phase of wound healing is integrin signaling. Integrins provide a mechanical connection between matrix components and are involved in the transmission of a variety of cell communication signals important in pathways such as angiogenesis and cell migration (Gailit and Clark, 1994; Katsumi et al., 2005). As mechanotransducers, integrins help to sense and transduce mechanical stresses, such as macro- and microstrain. Both of these types of strain are imparted to tissues when negative pressure is manifolded through Granu-Foam® Dressing during V.A.C.® Therapy (Saxena et al., 2004).

Wound Healing Phenotype and Genes.

Of clinical importance was the fact that wound area over the first two days of treatment differed significantly between treatment groups. The greatest reduction in wound area occurred in animals treated with V.A.C.®, while animals treated with GUS experienced an increase in wound area. The significant increase in size in wounds from GUS treated animals may be due to the fact that GUS has a negative impact on the early stages of wound healing in diabetic rats.

A goal of this study was to identify a "wound healing gene signature". This is of interest due to its potential as a prognostic indicator of successful wound healing.

When looking at gene relationships, it is not necessarily the number of genes which are most important, but rather how the patterns of uniquely expressed genes within a treatment group, along with differential fold changes of shared genes, correlate to a strong clinically relevant response. In the present study, this response is wound healing as assessed by wound area. In V.A.C.® treated animals, there was a large number of uniquely expressed genes, as well as shared genes, with higher fold changes. This gene signature correlated with a significantly greater decrease in wound area (FIG. 3). On the contrary, the uniquely expressed genes following GUS were associated with an increase in wound size. For the V.A.C.® treated group, there must be a unique gene signature which caused the wound area to decrease significantly by day 2 of healing.

The twelve genes potentially important to wound healing were chosen from pathways shown in Table 2, based on their higher fold changes in V.A.C.® Therapy compared to the other two groups. The gene targets selected were interleukin 6 (IL-6), chemokine ligand 7 (Ccl7), tissue inhibitor of metalloproteinase 1 (TIMP1), integrin alpha M (Itgam), suppressor of cytokine signaling 3 (Socs3), matrix metalloproteinase-8 (MMP-8), macrophage inflammatory protein-1 alpha receptor gene (MIP1R), toll like receptor 1 (TLR1), tumor necrosis factor receptor superfamily member 1b (Tnfrsf1b), heat shock protein 70 (Hsp70), calmodulin-like 3, and keratin complex 1 acidic gene 14 (Krt1-14) (Table 3). Each of these genes is known to play a role in successful wound healing.

Under subatmospheric pressure, the GranuFoam® Dressing used in V.A.C.® Therapy imparts both macrostrain and microstrain to tissue (Saxena et al., 2004). These micromechanical forces have been associated with cellular responses such as cell signaling. Recent research theorized that cells sense changes in their environment through expression of integrins such as Itgam (Smith et al., 2007). As shown in Table 3, following V.A.C.® Therapy, Itgam exhibited a 72.3% higher fold change than following MWH and a 372.2% higher fold change than following GUS.

IL-6, MIP1R, toll like receptor 1, and Socs3 are representative of various inflammatory pathways (as shown in Table 3) and are all associated with successful wound healing (Gallucci et al., 2000; Rakoff-Nahoum et al., 2004; DiPietro et al., 2007; Goren et al., 2006). Il-6 is involved in growth and differentiation of cell types. It has been shown that IL-6-knockout mice display significantly delayed cutaneous wound healing (Gallucci et al., 2000). It has also been shown that toll like receptor pathways can be activated by endogenous inflammatory stimuli (Li et al., 2001). A function of toll receptors is one of epithelial homeostasis and protection from epithelial injury. They may also directly induce the expression of factors including heat shock proteins, IL-6, and tumor necrosis factor which are involved in tissue repair and in protection of tissue from injury (Rakoff-Nahoum et al., 2004). Socs3 is a key modulator of cytokine signaling by proteins that attenuate signal transduction (Goren et al., 2006). In the current study, microarray results for Socs3 show that the gene was upregulated in V.A.C.® Therapy treated tissues 2.2 times higher than for MWH treated tissues and 4.2 times higher than for gauze under suction. It has previously been observed that an induction of Socs3 early upon skin injury provides a decrease in inflammatory potency of rapidly induced cytokines at the wound site (Goren et al., 2006; Kampfer et al., 2000). This corroborates previous proteomic results which indicated that V.A.C.® Therapy may function in part through modulation of the inflammatory response (Stechmiller et al., 2006). This modulation of the inflammatory response at the genomic level may then be one of the factors which led to the significant decrease in wound area seen in this study.

V.A.C.® Therapy promotes granulation tissue formation in both acute and chronic wounds, including complex diabetic foot wounds (Andros et al., 2006; Armstrong and Layery, 2005; McCallon et al., 2000; Eginton et al., 2003). The remaining members of the 12 genes identified herein may be involved in the production of this granulation tissue. Granulation tissue is mainly composed of extracellular matrix, endothelial cells and fibroblasts. Induction of Hsp70, a molecular chaperone, has been associated with the development of thermotolerance and protection against various stresses including hypoxia and ischemia (Kregel, 2002). Cells within the wound bed should contain significant amounts of inducible Hsp70 in an effort to maintain proper function within the healing wound (McMurtry et al., 1999) since cells must be maintained and protected from wound environment stresses during the early granulation phase.

MMP-8 is the predominant collagenase present in the early phases of acute, healing wounds. Excessive collagenolytic activity has been associated with reduced levels of TIMP1 in chronic wounds (Armstrong and Jude, 2002). In the current study levels of MMP-8 and TIMP1 mRNA were both greatly increased following 2 days of treatment with V.A.C.® Therapy. Following two days of treatment, TIMP1/MMP-8 ratios were 2.2 for V.A.C.®, 8.5 for MWH and 0.7 for GUS (Table 3). While extracellular matrix degradation is important for wound healing, excessive degradation via MMP-8 is associated with poor healing outcomes (Yager and Nwomeh, 1999). The high fold change increase observed for TIMP1 mRNA may be important for keeping wound proteolytic activity from becoming detrimental to the wound healing process.

CONCLUSIONS

Overall, more genes were upregulated and healing pathways over represented in tissues which had been treated with V.A.C.® Therapy than with the other two treatment modalities tested. Wound area was also decreased significantly in V.A.C.® treated animals.

REFERENCES

American Diabetes Association Diabetes Statistics Page, American Diabetes Web Site. Accessed Feb. 1, 2007.

Andros G, Armstrong D G, Attinger C E, Boulton A J, Frykberg R G, Joseph W S, et al. Consensus statement on negative pressure wound therapy (V.A.C. Therapy) for the management of diabetic foot wounds. Wounds 18[6], S1-S32. 2006.

Argenta L C, Morykwas M J. Vacuum-assisted closure: a new method for wound control and treatment: clinical experience. Ann Plast Surg 1997 June; 38(6):563-76.

Armstrong D G, Jude E B. The role of matrix metalloproteinases in wound healing. J Am Podiatr Med Assoc. 92[1], 12-18. 2002.

Armstrong D G, Layery L A, Diabetic Foot Study Consortium. Negative pressure wound therapy after partial diabetic foot amputation: a multicentre, randomised controlled trial. Lancet 366[9498], 1704-1710. 2005.

Benjamini Y, Hochberg Y. Controlling the false discovery rate: A practical and powerful approach to multiple testing. Royal Statistical Soc 1993 Jan. 1; 57(1):289-300.

Bolstad B M, Irizarry R A, Astrand M, Speed T P. A comparison of normalization methods for high density oligonucleotide array data based on variance and bias. Bioinformatics 2003 Jan. 22; 19(2):185-93.

Brem H, Sheehan P, Rosenberg H J, Schneider J S, Boulton A J M. Evidence-based protocol for diabetic foot ulcers. Plast Reconstr Surg 117, 193S-209S. 2006.

Bunka D and Stockley P G. Aptamers come of age—at last. Nat. Rev. Microbiol. 4, 588-596. 2006.

Centers for Disease Control National Diabetes Fact Sheet. CDC Web Site. Accessed Feb. 1, 2007.

Clark J B, Palmer C J, Shaw W N. The diabetic Zucker fatty rat. Proc Soc Exp Biol Med 173, 68-75. 1983.

Diegelmann R F, Evans M C. Wound Healing: An Overview of Acute, Fibrotic and Delayed Healing. Front Biosci 2004 Jan. 1; 9:283-9.

DiPietro L A, Burdick M, Low Q E, Kunkel S L, Strieter R M. MIP-1a as a critical macrophage chemoattractant in murine wound repair. J Clin Invest 101[8], 1693-1698.2007.

Eginton M T, Brown K R, Seabrook G R, Towne J B, Cambria R A. A prospective randomized evaluation of negative-pressure wound dressings for diabetic foot wounds. Ann Vasc Surg 2003; 17(6):645-9.

Franz S et al. Innate immunity and angiogenesis. Circ. Res. 96, 15-26. 2005.

Gailit J, Clark R A. Wound repair in the context of extracellular matrix. Curr Opin Cell Biol 6[5], 717-725. 1994.

Gallucci R M, Simeonova P P, Matheson J M, Kommineni C, Guriel J L, Sugawara T, et al. Impaired cutaneous wound healing in interleukin-6-deficient and immunosuppressed mice. FASEB J. 14, 2525-2531. 2000.

Goldman R. Growth factors and chronic wound healing: past, present, and future. Adv Skin Wound Care 2004; 17(1):24-35.

Goren I, Linke A, Muller E, Pfeilschifter J, Frank S. The suppressor of cytokine signaling-3 is upregulated in impaired skin repair: implications for keratinocyte proliferation. J Invest Dermatol 126, 477-485. 2006.

Harding K G, Morris H L, Patel G K. Science, medicine and the future: healing chronic wounds. BMJ 324[7330], 160-163. 2002.

IDF. Diabetes Atlas. 3rd ed. Brussels: International Diabetes Federation; 2005a.

IDF. Diabetes and foot care: time to act. Brussels: International Diabetes Federation; 2005b.

Jazag A et al. Single small-interfering RNA expression vector for silencing multiple transforming growth factor-β pathway components. Nucl. Acids Res. 33, e131. 2005.

Jeffcoate W J. The incidence of amputation in diabetes. Acta Chir Belg 2005 Apr. 1; 105(2):140-4.

Kampfer H, Muhl H, Manderscheid M, Kalina U, Kauschat D., Pfelschifter J, et al. Regulation of interleukin-18 (IL-18) expression in keratinocytes (HaCaT): implications for early wound healing. Eur Cytokine Netw 11, 626-633. 2000.

Katsumi A, Naoe T, Matsushits T, Kaibuchi K, Schwartz M A. Integrin activation and matrix binding mediate cellular responses to mechanical stretch. J Biol Chem 280(17), 16546-16549. 2005.

KCI Licensing. V.A.C. Therapy Clinical Guidelines. KCI Licensing; 2006.

Kim I Y et al. Transforming growth factor-β: Biology and clinical relevance. J Biochem Mol Biol 38, 1-8. 2005.

Kregel K C. Heat shock proteins: modifying factors in physiological stress responses and acquired thermotolerance. J Appl Physiol 92, 2177-2186. 2002.

Krützfeldt et al. Silencing of microRNAs in vivo with 'antagomirs.' Nature 438, 685-689. 2005.

Li M, Carpio D F, Zheng Y, Bruzzo P, Singh V, Ouaaz F, et al. An essential role of the NF-kappa B/Toll-like receptor pathway in induction of inflammatory and tissue-repair gene expression by necrotic cells. J Immunol 166[12], 7128-7135. 2001.

Li Q, Fukuda K, Lu Y, Nakamura Y, Chikama T, Kumagai N, et al. Enhancement by neutrophils of collagen degradation by corneal fibroblasts. J Leukoc Biol 74, 412-419. 2003.

McCallon S K, Knight C A, Valiulus J P, Cunningham M W, McCulloch J M, Farinas L P. Vacuum-assisted closure versus saline-moistened gauze in the healing of postoperative diabetic foot wounds.

McMurtry A L, Cho K, Young L J T, Nelson C F, Greenhalgh D G. Expression of HSP70 in healing wounds of diabetic and nondiabetic mice. J Surg Res 86, 36-41. 1999. Ostomy Wound Manage 2000 August; 46(8):28-32, 34.

Medina A, Scott P G, Ghahary A, Tredget E E. Pathophysiology of chronic nonhealing wounds. J Burn Care Rehabil 26[4], 306-319. 2005.

Meszaros A J, Reichner J S, Albina J E. Macrophage-induced neutrophil apoptosis. J Immunol 2000; 165(1):435-41.

Rakoff-Nahoum S. Paglino J, Eslami-Varzaneh F, Edberg S, Medzhitov R M. Recognition of commensal microflora by toll-like receptors is required for intestinal homeostasis. Cell 118, 229-241. 2004.

Reddi A H. Cartilage morphogenic proteins: role in joint development, homeostasis, and regeneration. Ann Rheum Dis 62(Suppl II), ii73-ii78. 2003.

Saxena V, Hwang C W, Huang S, Eichbaum Q, Ingber D E, Orgill D P. Vacuum-assisted closure: microdeformations of wounds and cell proliferation. Plast Reconstr Surg 114[5], 1086-1098. 2004.

Schultz G S, Ladwig G, Wysocki A. Extracellular matrix: review of its roles in acute and chronic wounds. World Wide Wounds 2005 Aug. 1; 1-24.

Searle A, Campbell R, Tallon D, fitzgerald A, Vedhara K. A qualitative approach to understanding the experience of ulceration and healing in the diabetic foot: Patient and podiatrist perspectives. Wounds 17[1], 16-26. 2005.

Sharman D. Moist wound healing: a review of evidence, application and outcome—Review. Diabetic Foot 6[3], 112-116. 2003.

Shilo S. et al. MicroRNA in cutaneous wound healing: A new paradigm. DNA Cell Biol. 26, 227-237. 2007.

Sibbald G, Orsted H, Schultz G S, Coutts P. Keast D. Preparing the wound bed 2003: Focus on infection and inflammation. Ostomy Wound Manage 49[11], 24-51. 2003.

Smith A P S, Kieswetter K, Goodwin A L, McNulty A. Negative Pressure Wound Therapy. In: Krasner D L, Rodeheaver G, Sibbald R G, editors. Chronic Wound Care: A clinical source book for healthcare professionals. 4th Edition ed. Malvern: HMP Communications; 2007. p. 271-86.

Stadelmann W K, Digenis A G, Tobin G R. Physiology and Healing Dynamics of Chronic Cutaneous Wounds. Am J Surg 1998 Aug. 24; 176(Suppl 2A):26S-38S.

Stechmiller J K, Kilpadi D V, Childress B, Schultz G S. Effect of V.A.C.® Therapy on the expression of TNF-a, IL-1, MMP-2, MMP-3 and TIMP-1 in wound fluid of adults with pressure ulcers. Wound Repair Regen in press. 2006.

Thomas P D, Campbell M J, Kejariwal A, Mi H, Karlak B, Daverman R, et al. PANTHER: a library of protein families and subfamilies indexed by function. Genome Res 2003 Sep. 1; 13(9):2129-41.

Thomas P D, Kejariwal A, Guo N, Mi H, Campbell M J, Muruganujan A, et al. Applications for protein sequence-function evolution data: mRNA/protein expression analysis and coding SNP scoring tools. Nucleic Acids Res 2006 Jul. 1; 34(Web Server Issue):W645-W650.

Venturi M L, Attinger C E, Mesbahi A N, Hess C L, Graw K S. Mechanisms and clinical applications of the vacuum-assisted closure (VAC) Device: a review. Am J Clin Dermatol 6[3], 185-194. 2006.

Wu L. et al. Keratinocyte growth factor induces granulation tissue in ischemic dermal wounds. Importance of epithlial-mesenchymal cell interactions. Arch Surg 131, 660-666. 1996.

Yager D R, Nwomeh B C. The proteolytic environment of chronic wounds. Wound Rep Reg 7[6], 433-441. 1999.

Zhou R-H et al. Vascular endothelial growth factor activation of sterol regulatory element binding protein. Circ. Res. 95, 471-478. 2004.

PCT Patent Publication WO06083182A1.
PCT Patent Publication WO06134494A2.
PCT Patent Publication WO9954456A1.
US Patent Publication US20070191273A1.

It should be apparent from the foregoing that an invention having significant advantages has been provided. While the invention is shown in only a few of its forms, it is not just limited but is susceptible to various changes and modifications without departing from the spirit thereof.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

We claim:

1. A method of treating a wound site in dermal tissue, the method comprising:
positioning at the wound site a reticulated open cell foam dressing having a plurality of flow channels, wherein the dressing is fluidly connected to a reduced pressure source; applying a nucleic acid to the dressing, wherein the nucleic acid is operably linked to a control element that directs expression of the nucleic acid inside a cell, and encodes a transcription factor selected from the group consisting of hypoxia-inducible factor 1-alpha (HIF-1α), homeobox protein HoxD3, and E-26 transformation-specific factor Net, promoting wound healing to the wound site; and applying reduced pressure from the reduced pressure source through the plurality of flow channels to the wound site for promoting wound healing, wherein the applying of the nucleic acid to the dressing is performed using a nucleic acid source fluidly connected to the dressing, and the method comprises alternating between the applying of reduced pressure and the applying the nucleic acid.

2. The method of claim 1 wherein the nucleic acid is applied to the dressing before positioning the dressing at the wound site.

3. The method of claim 1, wherein the dressing is a reticulated open cell polyurethane foam.

4. The method of claim 1, wherein the transcription factor is HIF-1α.

5. The method of claim 1, wherein the transcription factor is homeobox protein HoxD3.

* * * * *